US010781038B2

(12) United States Patent
Belda Mora

(10) Patent No.: US 10,781,038 B2
(45) Date of Patent: Sep. 22, 2020

(54) SYSTEM FOR CONTAINING MEDICAL WASTE WITH A BAG AND MACHINE FOR PRODUCING SAID BAG

(71) Applicant: STERIALE SOCIEDAD ANONIMA, Mortril (Granada) (ES)

(72) Inventor: Juan Manuel Belda Mora, Banyeres e Mariola (ES)

(73) Assignee: STERIALE SOCIEDAD ANONIMA, Motril (Granada) (ES)

( * ) Notice: Subject to any disclaimer, the term of this patent is extended or adjusted under 35 U.S.C. 154(b) by 239 days.

(21) Appl. No.: 16/073,280

(22) PCT Filed: Jan. 27, 2017

(86) PCT No.: PCT/ES2017/070046
§ 371 (c)(1),
(2) Date: Jul. 26, 2018

(87) PCT Pub. No.: WO2017/129848
PCT Pub. Date: Aug. 3, 2017

(65) Prior Publication Data
US 2019/0031437 A1    Jan. 31, 2019

(30) Foreign Application Priority Data

Jan. 27, 2016 (ES) .................. 201600070

(51) Int. Cl.
| B65F 1/16 | (2006.01) |
| B65F 1/06 | (2006.01) |
| B32B 27/32 | (2006.01) |
| A61B 50/36 | (2016.01) |

(Continued)

(52) U.S. Cl.
CPC .............. *B65F 1/06* (2013.01); *A61B 50/36* (2016.02); *A61L 2/07* (2013.01); *A61L 11/00* (2013.01);

(Continued)

(58) Field of Classification Search
CPC ...... B65F 1/06; B65F 1/00; B65F 1/16; B65F 7/00; A61B 50/36; A61L 11/00

(Continued)

(56) References Cited

U.S. PATENT DOCUMENTS

| 2,013,086 A | 9/1935 | Baker |
| 2,256,506 A | 9/1941 | Wagner |

(Continued)

FOREIGN PATENT DOCUMENTS

| EP | 0 624 378 A1 | 11/1994 |
| GB | 940316 A | 10/1963 |

(Continued)

OTHER PUBLICATIONS

International Search Report and Written Opinion dated May 4, 2017 Issued in International Application No. PCT/ES2017/070046.

*Primary Examiner* — King M Chu
(74) *Attorney, Agent, or Firm* — Knobbe, Martens, Olson & Bear, LLP

(57) ABSTRACT

The invention relates to a system for containing medical waste with a bag and a machine for producing said bag. It relates to a reusable, hermetically sealed, metal container for medical waste, with a bag and locks or latches, which prevent the lid from being opened until the waste inside the same has been sterilized by the pressurized steam of an autoclave. It also relates to said plastic bag made up of two or more layers of different physical properties, configured into a single body. Said bag is housed inside the aforementioned hermetically sealed container. It also relates to a machine for producing these bags with a winder, folder and several sealers using heat resistance inserted into conveyer belts.

2 Claims, 20 Drawing Sheets

(51) Int. Cl.
*B65F 7/00* (2006.01)
*A61L 2/07* (2006.01)
*B65F 1/00* (2006.01)
*B09B 3/00* (2006.01)
*A61L 11/00* (2006.01)
*B32B 27/08* (2006.01)
*A61B 50/00* (2016.01)
*A61L 2/26* (2006.01)
*A61B 50/30* (2016.01)

(52) U.S. Cl.
CPC ............... *B09B 3/00* (2013.01); *B32B 27/08* (2013.01); *B32B 27/32* (2013.01); *B65F 1/00* (2013.01); *B65F 1/16* (2013.01); *B65F 7/00* (2013.01); *A61B 2050/009* (2016.02); *A61B 2050/0062* (2016.02); *A61B 2050/0066* (2016.02); *A61B 2050/316* (2016.02); *A61L 2/26* (2013.01); *B32B 2250/242* (2013.01); *B32B 2439/06* (2013.01); *B65F 2001/1676* (2013.01); *B65F 2210/162* (2013.01); *Y02W 30/10* (2015.05)

(58) Field of Classification Search
USPC .................................................... 220/495.06
See application file for complete search history.

(56) References Cited

U.S. PATENT DOCUMENTS

| | | | |
|---|---|---|---|
| 3,097,618 A | | 7/1963 | Davis |
| 3,266,710 A | | 8/1966 | Reeves |
| 3,685,720 A | * | 8/1972 | Brady .................... B65D 75/66 |
| | | | 206/439 |
| 3,768,725 A | * | 10/1973 | Pilaro ...................... A61L 2/26 |
| | | | 206/439 |
| 5,222,600 A | | 6/1993 | Stoddard et al. |
| 5,823,340 A | | 10/1998 | Maihofer |
| 5,947,288 A | * | 9/1999 | Dykstra .................... A61L 2/26 |
| | | | 206/439 |
| 6,059,112 A | * | 5/2000 | Dykstra .................... A61L 2/26 |
| | | | 206/438 |
| 8,101,134 B2 | * | 1/2012 | Prokash .................... A61L 2/07 |
| | | | 422/28 |

FOREIGN PATENT DOCUMENTS

| | | |
|---|---|---|
| GB | 1161903 A | 8/1969 |
| GB | 1471361 A | 4/1977 |
| WO | WO 94/19028 A1 | 9/1994 |

* cited by examiner

107

108

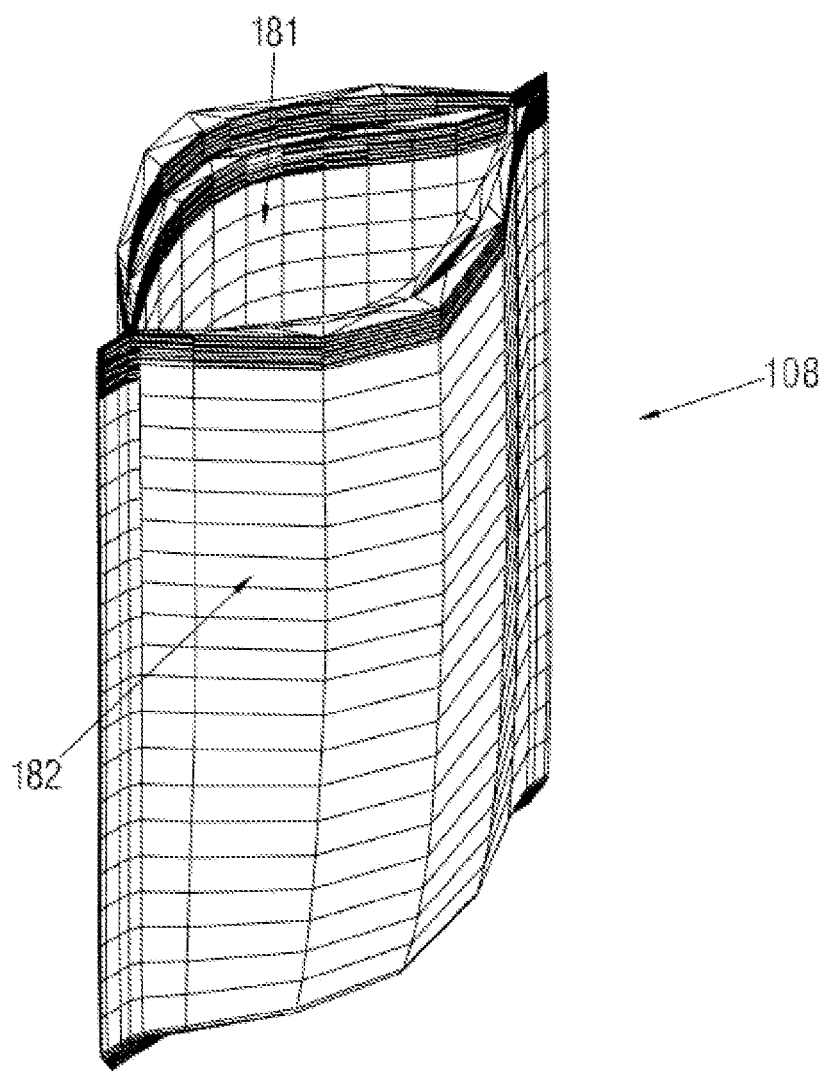

SYSTEM FOR CONTAINING MEDICAL WASTE WITH A BAG AND MACHINE FOR PRODUCING SAID BAG

CROSS-REFERENCE TO RELATED APPLICATIONS

This application is a 35 U.S.C. § 371 National Stage of PCT Application No. PCT/ES2017/070046 filed Jan. 27, 2017, which claims priority to Spanish Application No. ES 201600070 filed Jan. 27, 2016. The disclosures of each of these prior applications are hereby incorporated by reference herein.

The present invention relates to a hermetically sealed metal container with a device for opening the lid thereof only when the content inside the same has been sterilized by pressurized steam in an autoclave.

In another modality, the present invention relates to a plastic bag, made up of two different materials that are joined into a single body, each one having different physical properties, which is housed inside the aforementioned hermetically sealed container, since without this bag the hermetically sealed container herein described would not be functional.

Likewise, the present invention also relates to a system used for producing these bags by means of a heat-sealing machine on a conveyor belt, given that a considerable amount of time is needed to seal the bag by means of heat contact due to the composition of the different raw materials of the resulting bag.

More specifically, the invention proposes the development of a machine for producing double-layered plastic bags made of different compositions, which due to the particular arrangement thereof, allows double-layered bags to be achieved by means of heat sealing.

There is currently no container on the market for biomedical waste that, once hermetically closed for the transportation thereof, allows for the opening of the lid thereof to be able to carry out a pressurized steam sterilization inside an autoclave in a way that it is not done by external robotic action or by human action.

There are containers that, once closed, have a robotic or manual system for opening the lid thereof.

For the cleaning of these containers, once the content therein has been dumped, they must be cleaned either manually or by robots.

The bags are produced by guillotine-type sealing machines that make quick contact every time the contacts thereof are joined, sealing the bag by means of heat.

If a hermetically closed container is introduced inside a autoclave that uses pressurized steam, this container would not have the possibility of effectively sterilizing the content therein because, due to the fact that it is closed, it would not allow the steam to enter inside the same and sterilize the waste contained therein.

If an operator accidentally opened a container before sterilizing the waste inside, it could lead to hazardous waste being spilled or dumped into the environment.

Moreover, on the market are there no double-layered bags for medical waste that have the particularity of, on the one hand, compressing the waste and, on the other hand, keeping the containers clean from liquids or solids spilling inside the same.

When the bags are made up of highly dense materials, the sealing machine needs more exposure time for the contacts thereof to seal the bags through heat, and this slows its production due to this contact time.

To provide a solution to the aforementioned problems, the present invention comprises a system for containing medical waste with an opening for sterilization, of those commonly used for the heating and sterilization thereof inside a oven, which comprises a container and a lid, a double-layered bag housed inside the container and a mechanism for opening and closing the lid of the container; the container having an upper edge that is threaded; the lid being provided with a rubber sealing piece making the container airtight, a central inner shaft located in an axial position and arrangement, and a spring that runs the length of, and is concentric to, said central inner shaft and arranged on the downward side of the lid oriented towards the container, with a pushing piece on the free end of the spring and the central inner shaft being insertable into the bag; and the bag being double-layered, made up of two sub-bags, one of which is housed inside the other, both sub-bags being sealed on the lateral contours at the opening thereof, an inner sub-bag being made of LDPE heat-shrink material and the other outer sub-bag made of high-density polyethylene HDPE material; and the opening and closing mechanism of the lid of the container having opening and closing capability in accordance with the heat experienced inside the oven.

Preferably, the opening and closing mechanism of the lid of the container comprises two metal rods in a vertical arrangement, two holes in the upper region of the wall of the container, two lower latches-openings on the lid, another two circular latches also on the lid, a stop on the periphery of the container on the upper region thereof and adjacent to the upper threaded edge enabled of the same container; said metal rods arranged diametrically opposite on the wall of the container and contiguous on the upper end thereof to the holes of the container and secured and fastened on the lower end thereof to the inner vertical wall of the lower region of the container, said metal rods having the greater part of the longitudinal extension thereof being separated from and without making contact with said inner vertical wall of the container, and also being provided with protrusions on the upper end thereof of suitable dimensions for the passage thereof through the contiguous hole of the wall of the container and also provided with a suitable flexibility to move close to the inner vertical wall of the container when they are subjected to the necessary force; and the two lower latches-openings being diametrically opposite and fixed to the lid, and the other two circular locks also being diametrically opposite and fixed to the lid and at a higher position in relation to the two latches-openings and both pairs of elements separated by an angle approximately 20 degrees from a plan view of the lid.

For the same purpose, the present invention also comprises a machine for producing double-layered plastic bags that comprises:

a. Unrolled supply means of a first sheet of a first plastic material, b. Unrolled supply means of a second sheet of a second plastic material.

c. Positioning means for the two aforementioned sheets and with folding and bending capability, as well as ability to convert the positioning of said sheets into a linear, bent and continuous arrangement in a linear laminar assembly made up of two contiguous and overlapping central sheets as a result of a bending and folding of the first sheet over itself and by another two outer sheets resulting from another bending and folding of the second sheet over itself, the two outer sheets being arranged one on each side and contiguous to the other two central sheets.

d. Two rotating roller systems symmetrically arranged above and below, respectively, the aforementioned resulting linear laminar assembly, which in turn comprise:

a) Conveyor belts with a continuous strip, each one arranged on each roller system and actuated in the movement thereof by the same, and therefore also in a symmetric position on top of and below the aforementioned resulting linear laminar assembly, such that a section of the continuous cyclical movement is parallel and adjacent to said linear laminar assembly.

b) A plurality of heat sealers inserted in each conveyor belt and integral with the same in the movement thereof, and also symmetrically arranged above and below the aforementioned linear laminar assembly and arranged such that each heat sealer of a conveyor belt is in an adjacent and contiguous position with the other heat sealer of the other conveyor belt when, as a result of the continuous and cyclical movement of the conveyor belts, said heat sealers move along the section of continuous cyclical movement of the conveyor belts which is parallel and adjacent to the linear laminar assembly, which furthermore means that on said section the heat sealers simultaneously make contact with the linear laminar assembly from each one of the opposite sides of the same linear laminar assembly.

Preferably, the first sheet is made of low-density polyethylene (LDPE) heat shrink material and the second sheet is made of high-density polyethylene (HDPE).

More preferably, the heat sealers are electric.

The present invention is novel in that by merely detecting the heat of the steam autoclave, the container, given that it houses a special two-layer bag on the inside thereof, allows the first layer of the bag to be compressed due to the composition of the memory of the heat-shrink raw material thereof, thereby releasing metal rods that prevent the opening of the lid of the container and which are in contact with the bag.

This way, there is no possibility for the container to accidentally open unless there is a high temperature inside the same that makes the bag compress by the effect of the heat shrink memory and thus, when the waste receives this heat, the same becomes sterilized.

The bags have a second layer that does not allow liquids or waste to be spilled inside the container and thereby keeps the container clean without the need for a cleaning maintenance.

The present invention contributes to solving the present problem since it allows for a prolonged exposure of the contacts to seal the high-density bags, thereby achieving a large-scale production in a short amount of time.

More specifically, the present invention discloses a machine that seals bags by heat through a system of contact of the sealers with the bag by means of a conveyor belt, which allows the aforementioned prolonged exposure of the contacts to take place in order to seal the high-density bags, as well as achieving the aforementioned large scale production in a short amount of time.

The present invention describes a reusable, metal container for sterilizing medical waste with an opening system for the lid thereof only by the compression of the bag inside the same which, due to the effect of the temperature and by being in contact with metal rods, when said rods pivot on the lower shaft thereof, they will release latches on the lid.

More specifically, the present invention also discloses a reusable container for medical waste that comprises:

at least a metal vat with inner metal rods that pivot on the base thereof.

at least a metal vat which on the upper edge thereof has a threaded form to allow the lid to be screwed to the same.

at least a metal lid with fixed lower latches and other intermediate latches, which prevent the opening of the same, while the metal rods of the vat are in the closed position thereof, at least a silicone rubber piece on the lid with the objective of sealing the lid to the bag housed inside the vat and make the container sealed.

at least a filter made of a porous material housed in the lid which does not allow solid waste to exit the outside of the container.

at least a spring housed in the lid which allows for the opening of the same when it is compressed by releasing the intermediate lock.

at least a double-layered bag, made up of different materials for hospital waste. at least a metal shaft with a pusher housed in the center of the lid that allows the bag of waste to be inserted by compressing.

at least a winding and roller machine with the function of joining layers of different plastics into a single bag.

at least a heat sealing machine with the function in that by means of a conveyor belt it seals several bags at the same time by means of resistance.

Preferably, inside the metal vat there are two metal rods that will pivot or oscillate from the base thereof either outwardly or inwardly in the upper part of the vat, allowing the lid of the container to lock or unlock.

Furthermore, in the upper part of the vat, the material thereof is unfolded, ending in an inclined plane going from a smaller to a greater surface section, providing a threaded form to the outer edge of the vat.

The container of the present invention can comprise a lid in which an intermediate latch is housed, which has the function of screwing to the upper edge of the vat to hermetically seal it when reaching the end of its path.

The container can also comprise a lid in which an intermediate latch is housed, which has the function of a lock for the partial opening of the lid.

The container can also comprise a lid in which a filter is housed on the upper part thereof to retain solid particles and allow the entrance of steam into the inside of the vat once the intermediate latch is released.

The container can also comprise a lid in which a lower latch is housed which has the function of preventing the complete opening of the lid when the intermediate latch is released, thereby containing the waste of the inner bag.

The container can also comprise a lid in which there is a spring on the inside thereof, the function of which is to expel the lid outwards when the latches are released.

The container can also comprise a lid in which there is a rigid shaft inside the same, the function of which is for the bag of waste to remain inserted when compressed on this shaft, thereby avoiding direct manipulation by the operator.

Preferably the container can also comprise a lid in which on the rigid shaft thereof, there is a mobile platform, which moves in the direction of the same, allowing bag inserted on said shaft to be expelled by the action of the spring.

Also housed on the inside of the lid is a silicone rubber piece for the purpose of sealing the lid to the bag housed inside the vat and making it airtight.

The present invention also describes that housed in the lid of this container is a filter made of a porous material which does not allow solid waste to exit the outside of the vat.

In this invention said lid has lower and intermediate double latches, which will serve as guides on the threading housed on the upper edge of the vat for hermetically sealing the same; and by receiving the heat, the inner bag will compress, making the metal rods which are in contact with the bag pivot towards the inside of the vat and release the closing latches of the lid and by the effect of the compressed spring housed inside the lid, expel it towards the outside, allowing steam to enter to the inside of the bag and thereby sterilize the waste.

The present invention also discloses the bag for medical waste of the system/container object of the present invention, characterized in that it is made up of two different layers of raw material, consisting of:

at least an inner layer made up of heat shrink material with compression memory when receiving heat to reduce the volume of the waste inside the same.

at least an outer layer made up of high-density plastic material for retaining liquids or waste and making it so the container does not have to be cleaned.

Likewise, in the present invention a double-layered bag is described, the functions of which are, in the first layer, that of compressing the waste since the composition of the raw material thereof is heat shrink LDPE, and by receiving a temperature of 120 degrees Celsius or above, it has the physical properties of compressing and returning to the initial state thereof when produced (it has heat shrink memory) and this way compresses to ⅓ of the volume thereof. The purpose of the second layer of the bag is to seal the container with the lid, such that it is hermetically sealed. Likewise, this second layer of the bag prevents the liquids created inside the same from spilling inside the container, keeping it clean.

The present invention also relates to a winding/sealing machine, the purpose of which is to join the plastic layers of different compositions and seal the high-density bags by means of heat, allowing the process of the heat sealer of contacting the plastic parts of the bags to be more prolonged for an improved sealing without reducing the production speed of the bags.

The winding and folding machine object of the present invention is characterized in that it comprises different rollers which, in the different conjugations thereof, join two layers of different materials to combine them into a single plastic bag with two different properties.

The sealing machine which uses heat resistance according to the present invention can have two conveyor belts on which several sealers using heat resistance are anchored, which by sealing the bags on one of the two faces thereof also reduces the fusion and sealing time of each bag.

Preferably, the two conveyor belts, to which several sealers using heat resistance are anchored, seal the two layers of the bags on the sides thereof by means of heat, ¾ of the length of the same.

Also, the two conveyor belts in which several sealers using heat resistance are anchored preferably adapt the rhythm of the sealing and production of the bags, by determining the length of said conveyor belt and the number of sealers in the same, since the sealing time is constant.

Thanks to the present invention, a machine is achieved that is able to join the plastic layers of different compositions and seal the high density bags by means of heat, allowing the contact process of the heat sealer between the plastic parts of the bags to be more prolonged for an improved sealing without reducing the production speed of the bag.

Other characteristics and advantages of the machine for producing double-layered plastic bags will be evident from the description of a preferred, but not exclusive, embodiment, which is illustrated by way of non-limiting example in the accompanying drawings, wherein:

In a first modality the container herein described is made up of a lid (2) and a vat (1), both being metal.

The upper edge of the vat bends the excess material of the metal body towards the outside to give it an outer downward inclined curvature with a threaded-type end so that the lid can screw to the vat (FIG. 3). Also inside this vat, there are two metal rods (11a and 11b), the function of which is to oscillate from the lower shaft thereof toward the inside or outside of the container (1) through the holes (12), allowing the lid to be anchored with the latches thereof to the container when the metal rods are in the pivoting position towards the outside of the container (closed position) or in the pivoting position towards the inside of the container (open position) (FIGS. 14 and 15).

The placement of the lid on the vat allows the screwing and hermetic sealing thereof. This is achieved since on the periphery of the lid two lower fixed opposite latches (21) and another two intermediate opposite circular latches (22) are housed. Likewise, inserted inside the same is a metal shaft (23) on which a spring (24) moves, the spring being coupled to a piece that is also metal and acts as a pusher (25). Inside the lid a silicone rubber pieces is housed for the hermetic sealing (26) thereof, as well as a filter (27) to prevent the waste from exiting the container as shown in FIG. 4. The bags of waste will be inserted in the rod of the metal shaft on which the spring moves FIG. 19.

Once the lid is placed, the first latch of the same (21) coinciding with the entrance of the metal rods 11a and 11b (FIG. 10), the same will rotate in a clockwise direction 20 degrees, an then the lid will lower a few centimeters until the latches 22 enter through the entrance of the metal rods 11a and 11b (FIG. 11), the lid will then rotate 160 degrees in a clockwise direction screwing these latches 22 (FIG. 12) in the thread of the upper edge of the vat until reaching a stop 13, as shown in FIG. 13. At that moment, due to the effect of the thread between the lid and the vat, the container will be hermetically closed.

In another modality, the present invention also relates to a plastic bag (3) made up of two inner bags (sub-bags) sealed on the lateral contours thereof, which have different structural chemical compositions, such that the inner bag (31) is made up of LDPE heat shrink material and the outer bag (32) is made of up high-density polypropylene (HDPE) material (FIG. 23). Placed inside this bag is medical waste, such as gauze, gloves, infected plastic pieces, infectious materials, etc. (FIG. 6).

In another modality, the present invention also relates to a machine, the purpose of which is to produce double-layered bags. To do so, it uses several rollers (218) that in the different positions thereof, allow different materials such as low-density polypropylene (LDPE) heat shrink materials to be joined to other high-density polypropylene (HDPE) materials in a single double-layered bag. Said machine is novel in that it makes conveyor belts (164, 165) rotate by means of the inner rollers (221) thereof, which have different electric heat sealers (106) inserted which, by frontally coinciding, join the different high density plastic layers. This allows the heat sealer's process of contact between the different plastic parts of the bags to be more prolonged for an improved sealing without reducing the production speed of the bag (FIGS. 20 to 27).

For a greater understanding of the invention, drawings of an embodiment object of the present invention are attached as an explanatory, non-limiting example thereof.

FIGS. 26 and 27 are schematic views and from different perspectives of a plastic double-layered bag resulting from a preferred embodiment of the machine for producing plastic double-layered bags of the present invention.

Figure 1:
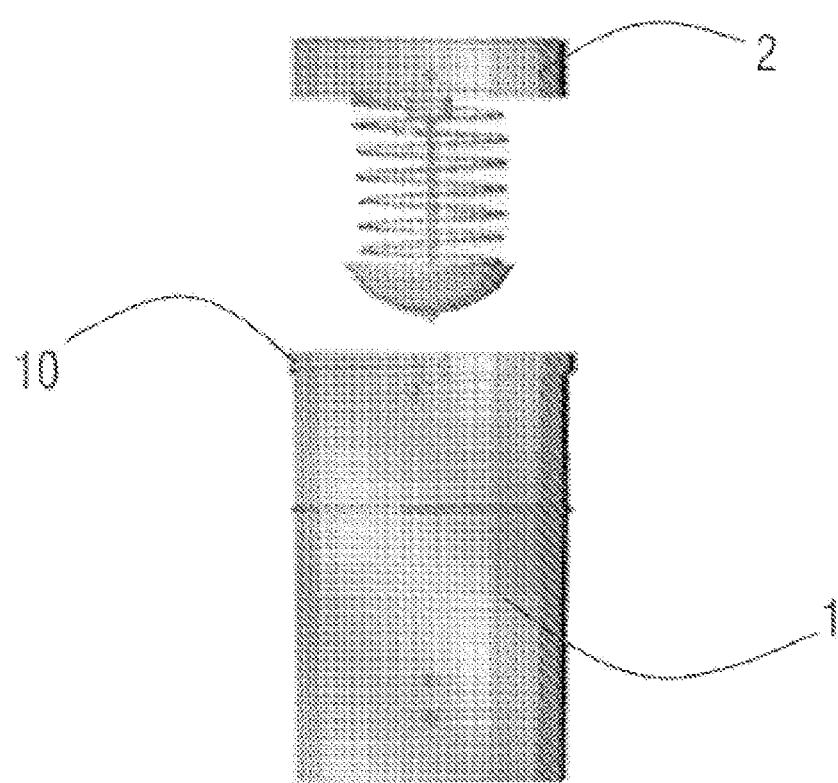
FIG. 1 is an elevation view of an embodiment of the container according to the present invention.
Figure 2:
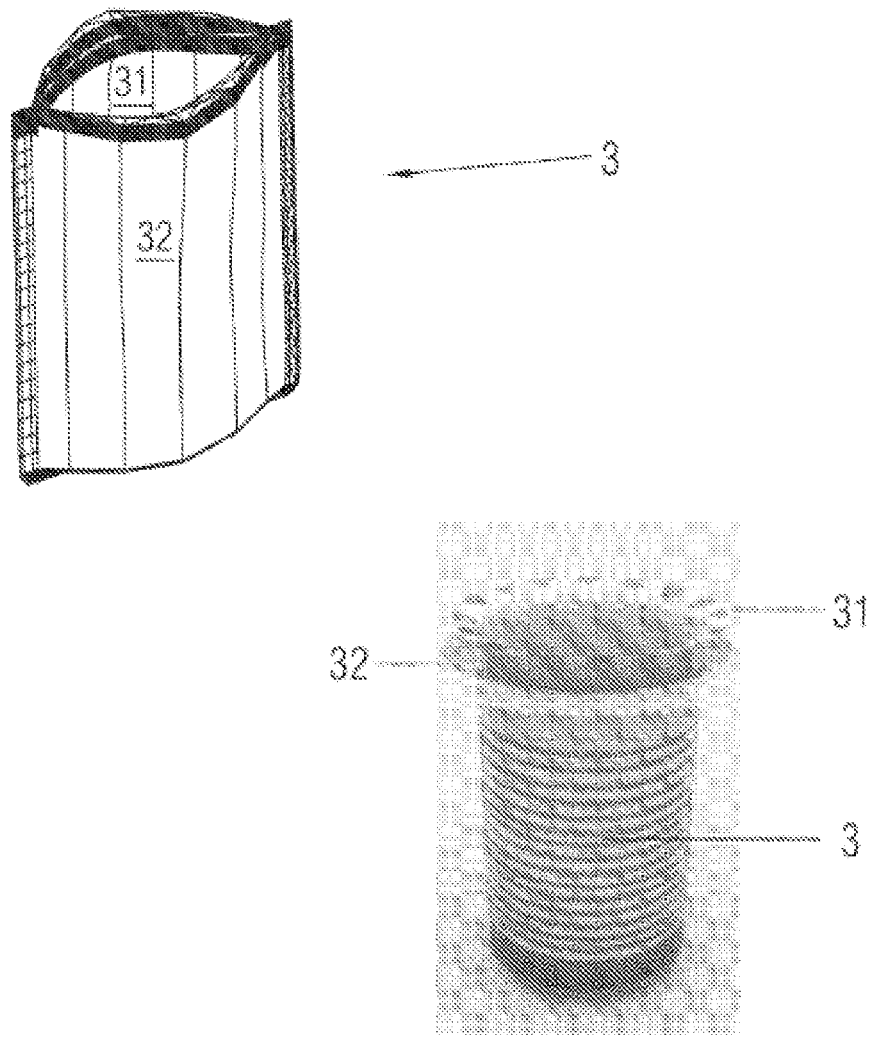
FIG. 2 shows two schematic views of two possible embodiments of the bag according to the present invention.

In a first modality, in the present invention a metal container is described that is made up of two bodies, a lid (2) and a vat (1) (FIG. 1). Inside the container a double-layered plastic bag (3) is placed, into which medical waste is placed. The first inner layer of the plastic bag is made up of LDPE heat shrink material (31) and the second outer layer is made up of HDPE (32) (FIG. 2).

Once the waste is placed in the double-layered bag (FIG. 6), the bag is then closed by the first LDPE heat shrink layer (FIG. 7); the second layer of the HDPE bag will be fixed in the initial open position thereof. The lid is screwed on the container, the bag of the first LDPE layer (FIG. 8) compressing the spring, and in turn, since this first layer is in contact with the metal rods (11a and 11b), they will pivot or oscillate toward the outside of the vat, obstructing the exit of the latches (22) of the lid as indicated in FIG. 13.

Figure 4:
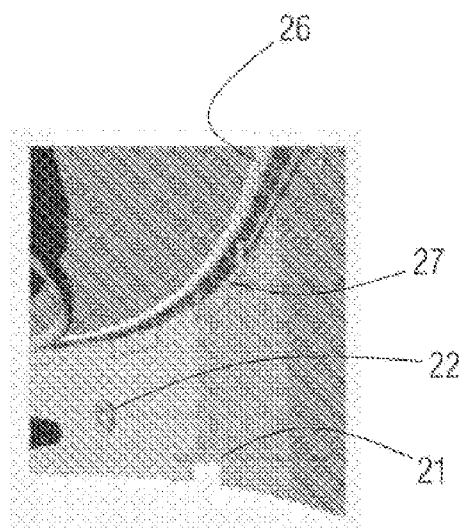
FIG. 4 is a detailed view of a part of the lid of the container, on the inner part thereof.
Figure 5:
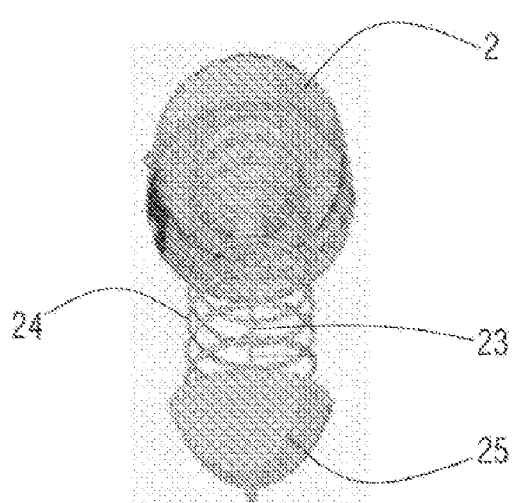
FIG. 5 is a schematic view of the lid of the container, seen from below.
Figure 8:
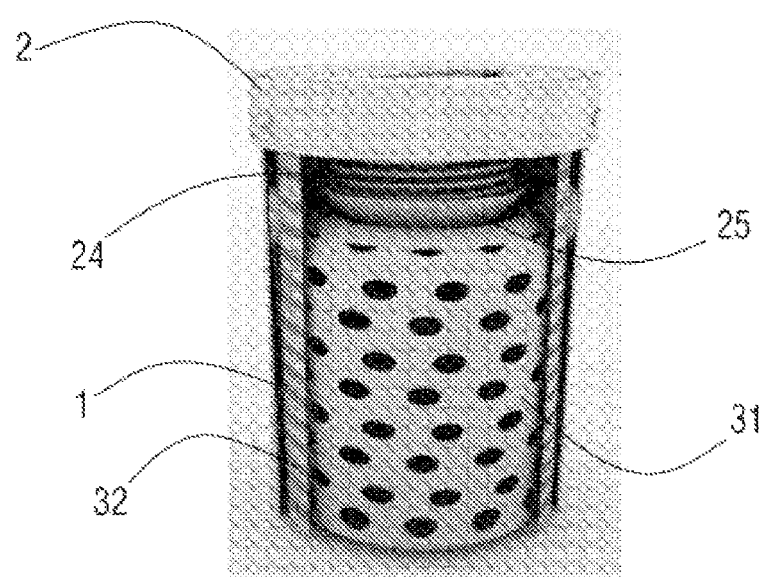
FIG. 8 is a view of the container, with the lid closed, in which the container has been partially cut to be able to see inside the same.
Figure 9:
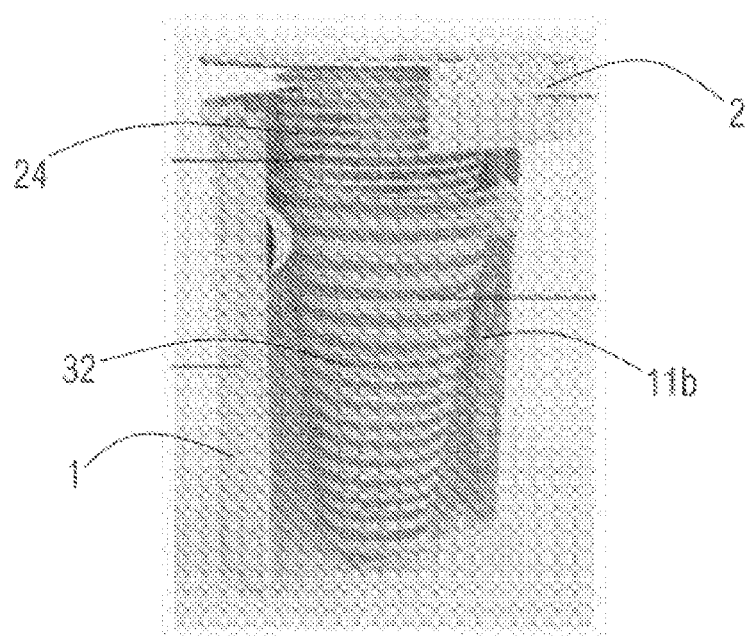
FIG. 9 is likewise a partial cross-sectional view of the system object of the present invention, with the lid in the open position.
Figure 10:
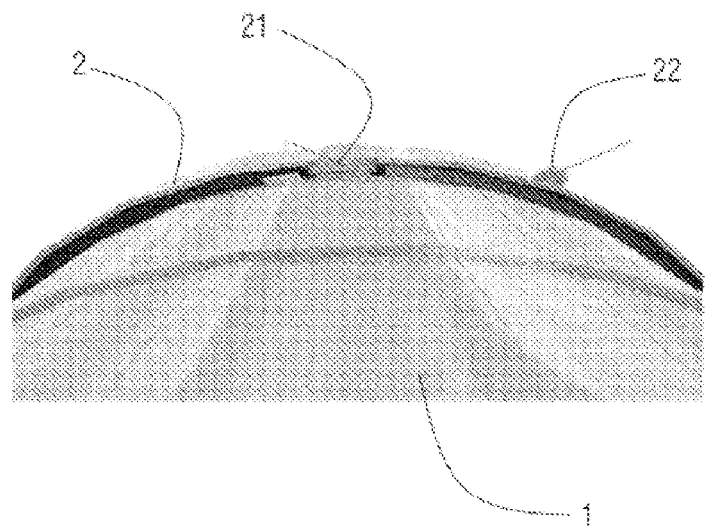
FIGS. 10 to 17 show the opening and closing process of the system object of the present invention.
Figure 11:
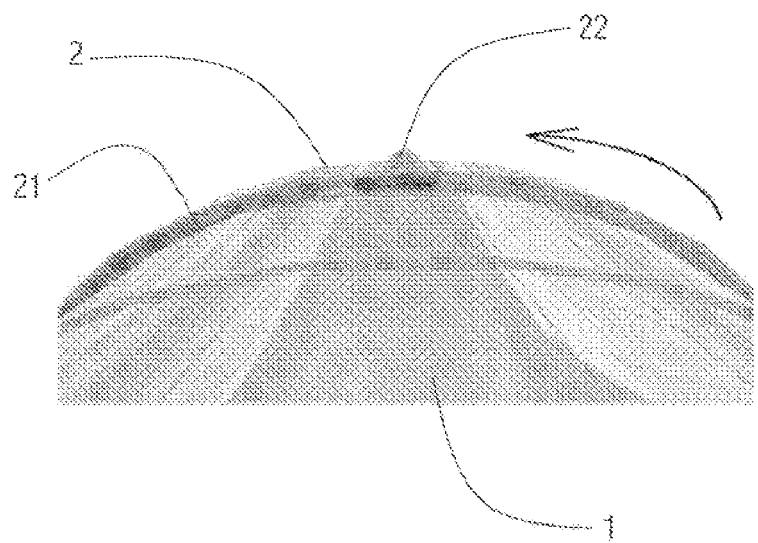
Figure 12:
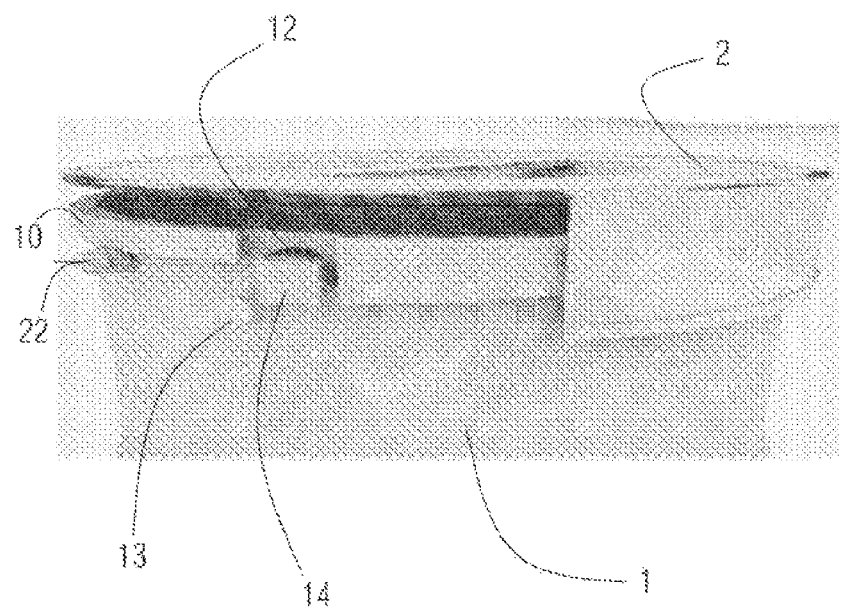

The placement of the lid on the vat, allows the screwing and hermetic sealing thereof. This is achieved since on the periphery of the lid two lower fixed opposite latches (21) and another two intermediate opposite circular latches (22) are housed (FIGS. 4 and 5). The first lower latches of the lid (21) slide through the entrance of the metal rods 11a and 11b of the vat as shown in FIG. 10, and the same will rotate in a clockwise direction 20 degrees. The lid will then lower a few centimeters until the latches 22 also enter through the entrance of the metal rods 11a and 11b (FIG. 11). The lid will then rotate 160 degrees in a clockwise direction, the round latches 22 screwing into the thread of the upper edge of the vat FIG. 12, until reaching the stop 13 as shown in FIG. 13. At this moment, by the effect of the thread between the lid and the vat, the container will remain hermetically closed by the silicone rubber piece (26) as shown in FIGS. 8 and 13.

Figure 14:
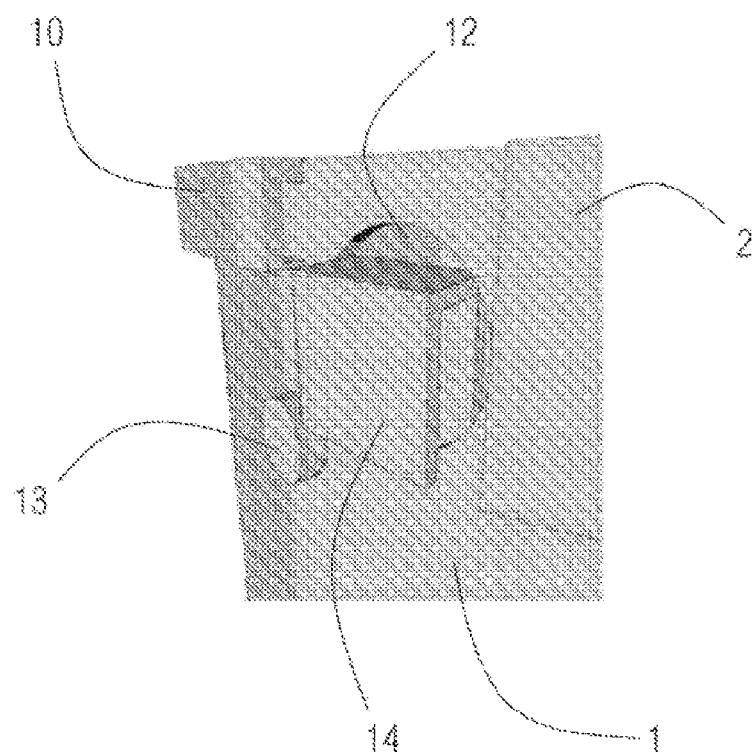
Figure 14A:
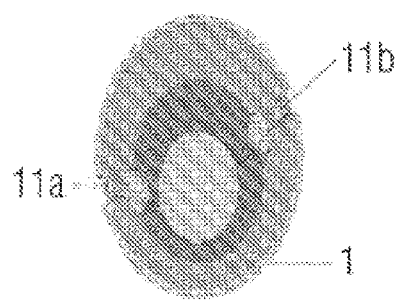

Since the waste contained inside the first layer of the LDPE bag is pressed by the action of the spring of the lid (24), the metal rods (11a and 11b) will be oscillated outwardly by the pressure of the bag in a closed position (FIGS. 14 and 14a).

Figure 13:
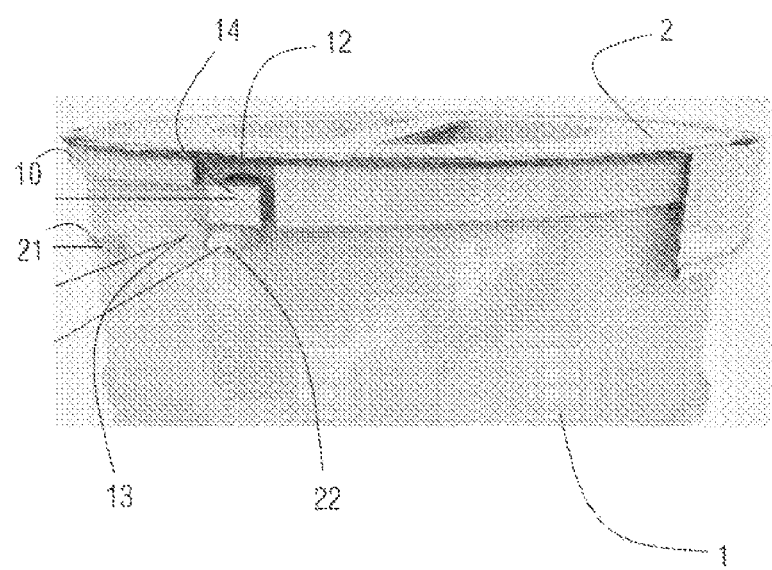

This closed positions prevents the lid (2) from opening, while the rods (11a and 11b) are in this mode (FIG. 13).

Figure 15:
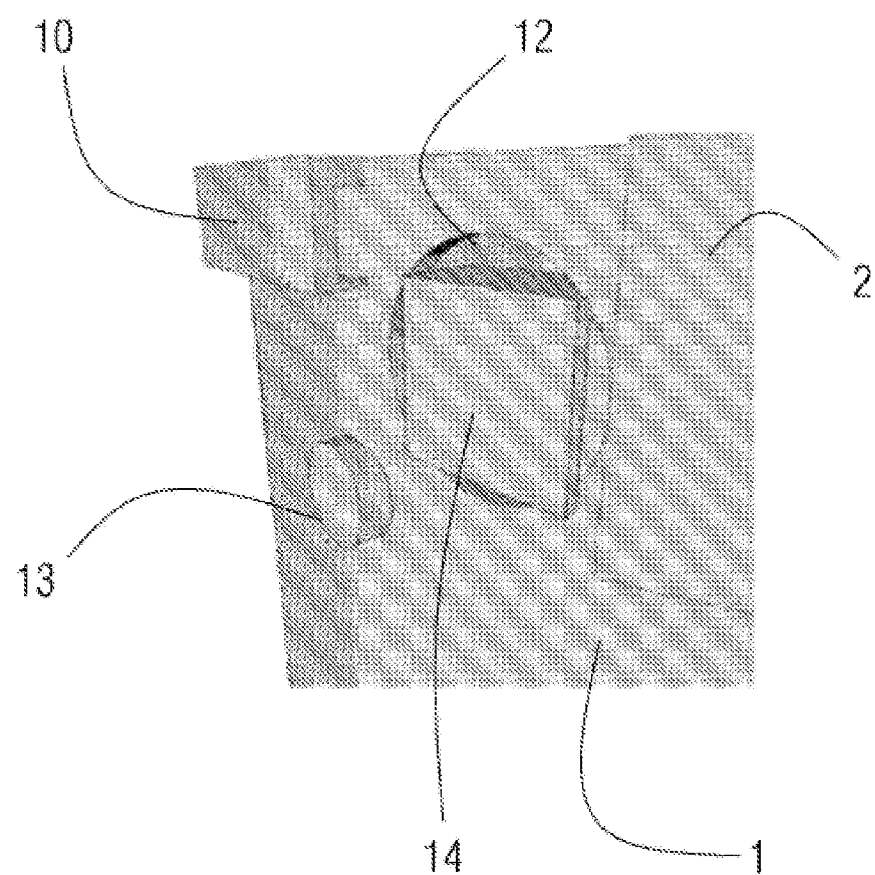
Figure 16:
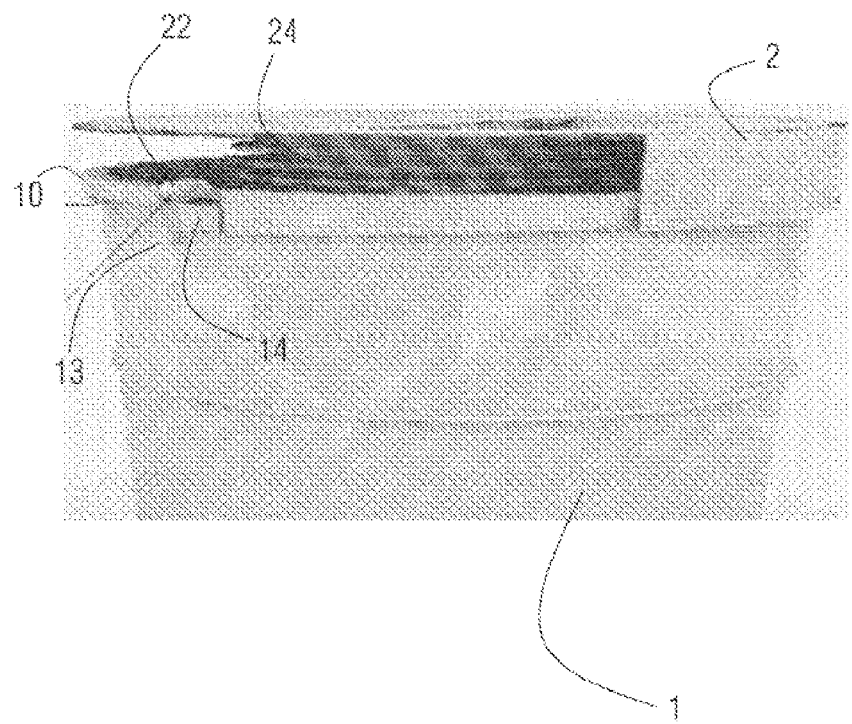

By the autoclave sterilizing the waste with pressurized steam and with the high temperature inside of the chamber of the autoclave, the bag of the first LDPE layer housed inside the container will compress by the heat shrink memory in diameter, causing the metal rods (11a-11b) that are in contact with the same to oscillate or pivot towards the inside of the vat, since the bag will no longer press the metal rods, as shown in FIGS. 15 and 16.

Once the metal rods pivot toward the inside of the vat, the lid with its round intermediate latches (22) will be released and by the action of the spring of the lid, the same will move upwards, until the lower and opposite latches (21) are anchored in the lower part of the thread of the upper edge of the vat FIG. 16. This allows the steam of the autoclave to enter inside the container through the upper holes of the lid (31), since there is no hermetic seal, thereby allowing the sterilization of the waste contained in the inner bag of the vat to take place.

A particle filter is housed in the upper part, which does not allow solid waste inside the bag to exit.

Once the sterilization cycle of the autoclave has finished, the container is then extracted from the chamber of the autoclave. We then rotate the lid 20 degrees in a counter-clockwise direction to release the lower latch from the lid (21) FIG. 17; since this latch prevents the opening of the lid given that they are anchored to the lower part of the thread of the upper edge of the vat when the intermediate latches were previously released (22) FIG. 17.

Figure 17:
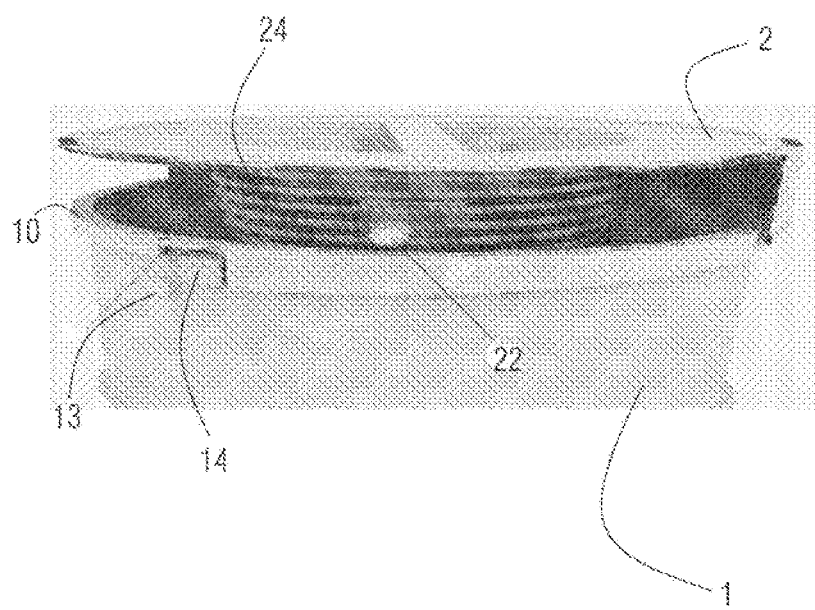
Figure 18:
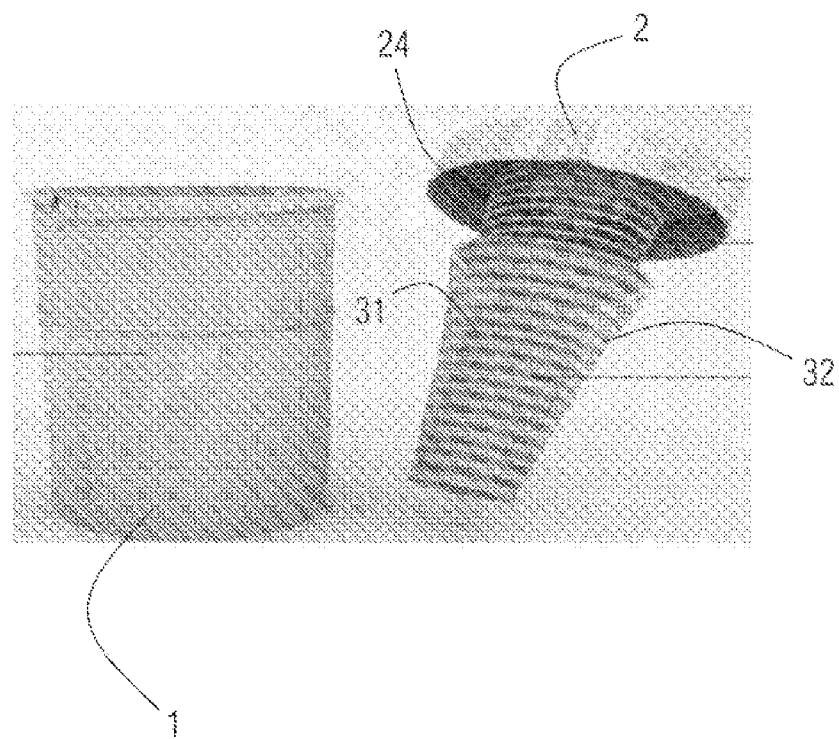
FIGS. 18 and 19 show the container, bag and lid of the container in different positions.

Anchored inside the lid is a metal shaft (23) on which a spring (24) moves coupled to a piece that is also metal and acts as a pusher (25) FIG. 5. The bags of the waste are anchored to the rod of the metal shaft on which the spring moves, since this shaft is inserted in the bag, (FIGS. 17 and 18).

Figure 19:
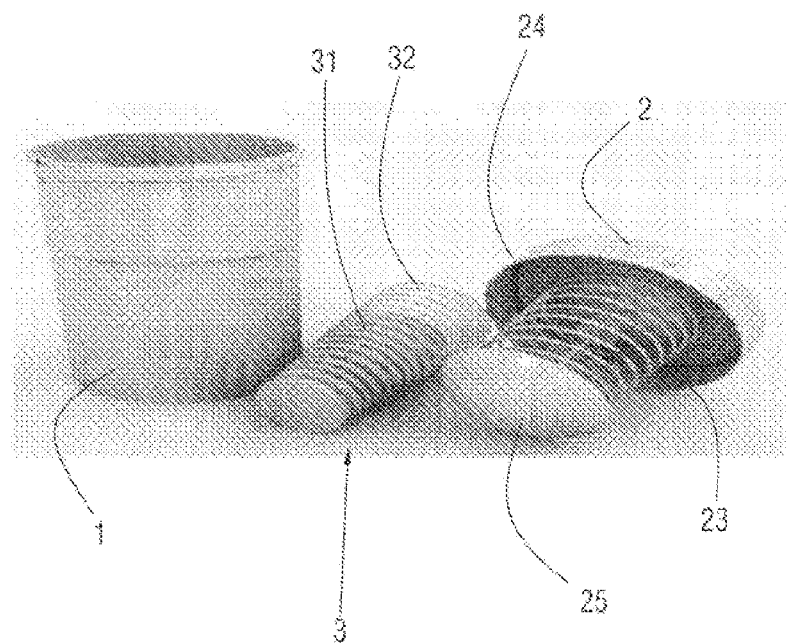

The spring of the lid will end up expelling the bag of the compressed waste by the action of the metal piece of the pusher (25), the shaft (23) being released (FIG. 19).

In a second modality, the present invention describes a double-layered bag (3) (FIG. 2), the properties of which are:

1. —In the inner layer thereof, that of compressing the waste given that the composition of the raw material thereof is LDPE heat shrink material (31), and by receiving heat and increase the temperature thereof, it has the physical properties of compressing and returning to the initial state of production thereof (it has heat shrink memory) and this way compresses to ⅓ of the initial volume thereof, or that of the waste it contains inside the same. 2. —On the outer layer of the bag made up of high-density polypropylene (HDPE) (32), it prevents the liquids formed inside the same from spilling into the container, keeping it clean. This outer layer has the purpose of being sealed with the rubber piece (26) of the lid of the container, such that it provides a hermetic seal between the bag and the lid (FIG. 8).

Figure 6:
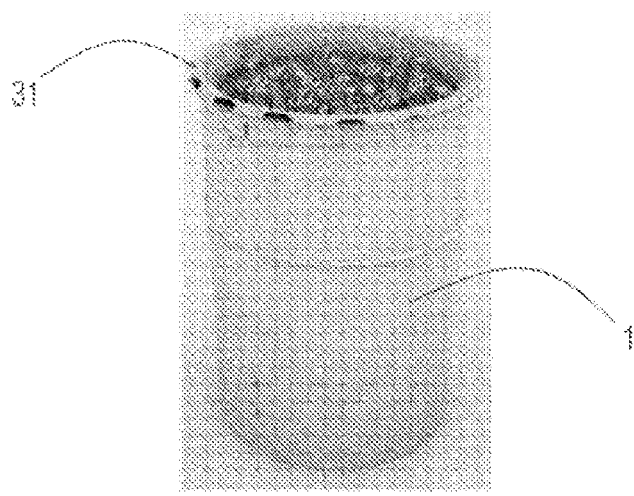
FIG. 6 is a view of the container, full, wherein neither the bag nor the lid has been shown in order to be able to observe the content thereof.
Figure 7:
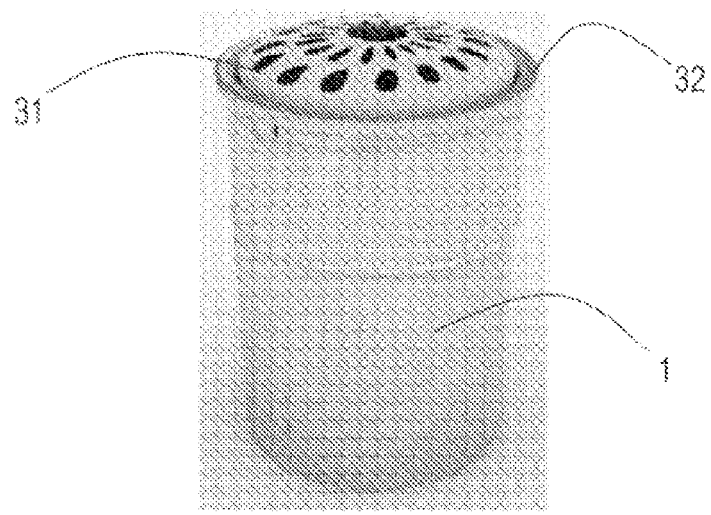
FIG. 7 is a view of the container, without the lid, and the bag object of the present invention.

Placed inside this bag (23) is the medical waste, such as gauze, gloves, infected plastic pieces, infectious materials, etc. (FIG. 6, 26, 27).

Figure 20:
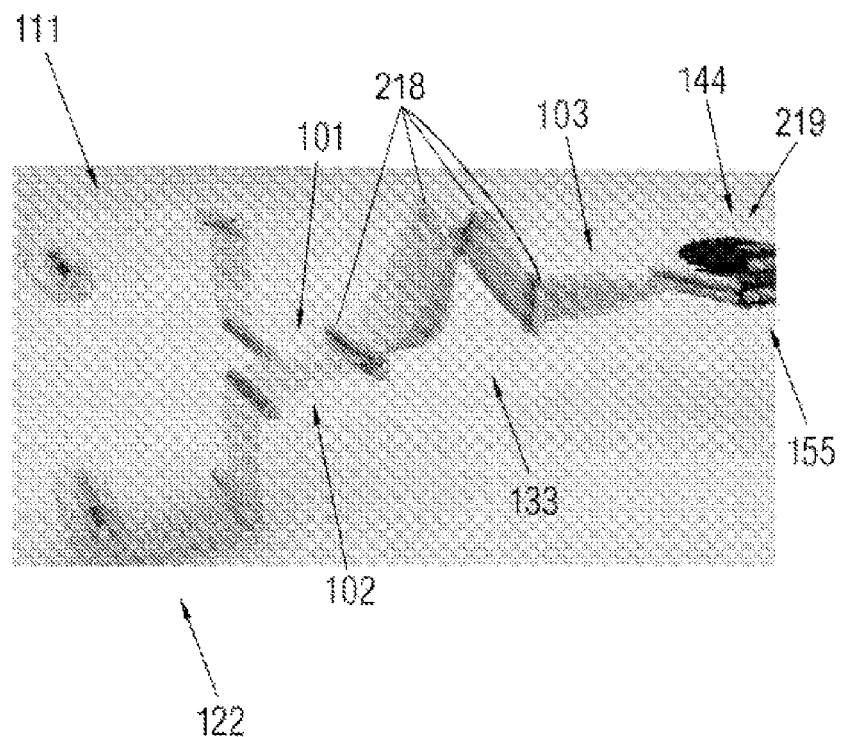
FIG. 20 is a schematic view of a preferred embodiment of the machine for producing plastic double-layered bags of the present invention.
Figure 21:
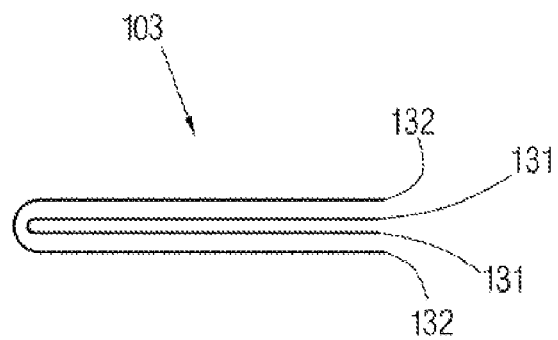
FIG. 21 is a schematic view of a cross section of the linear laminar assembly in a preferred embodiment of the machine for producing plastic double-layered bags of the present invention.

Both layers of the two bags are heat sealed on the sides thereof, joining them into a single body as shown in FIGS. 2, 20 and 27.

Figure 25:
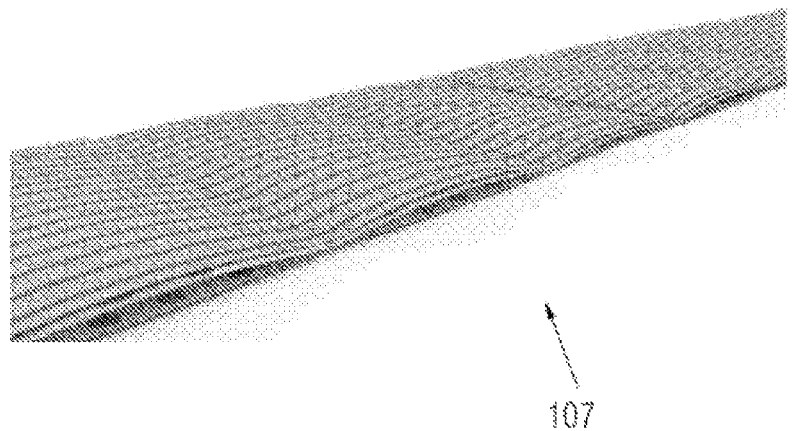
FIG. 25 is a schematic view of a laminar strip which results from the sealing process in a preferred embodiment of the machine for producing plastic double-layered bags of the present invention.
Figure 26:
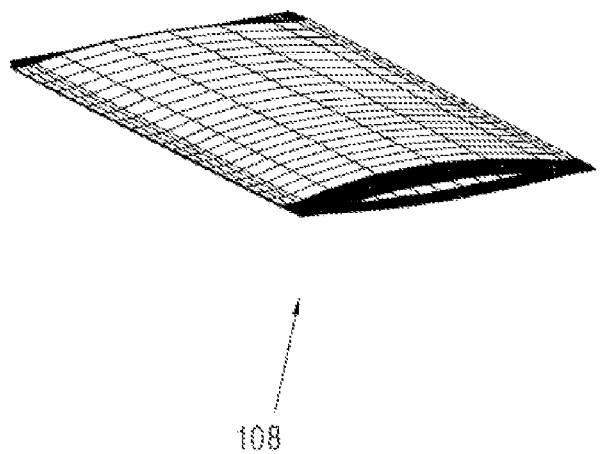

In a third modality, the present invention describes a series of rollers (218), which by being anchored in different positions, allow two layers of a different chemical composition to be joined, wherein the first inner layer or first inner sheet 101 of the plastic bag is made up of LDPE heat shrink material and the second outer layer or second sheet 102 is made up of HDPE (FIG. 25). Once the two layers are joined, they will form a plastic sheet which, after having passed through the sealer (219) FIG. 20, will end up forming the double-layered bags (107) (FIG. 25).

Figure 22:
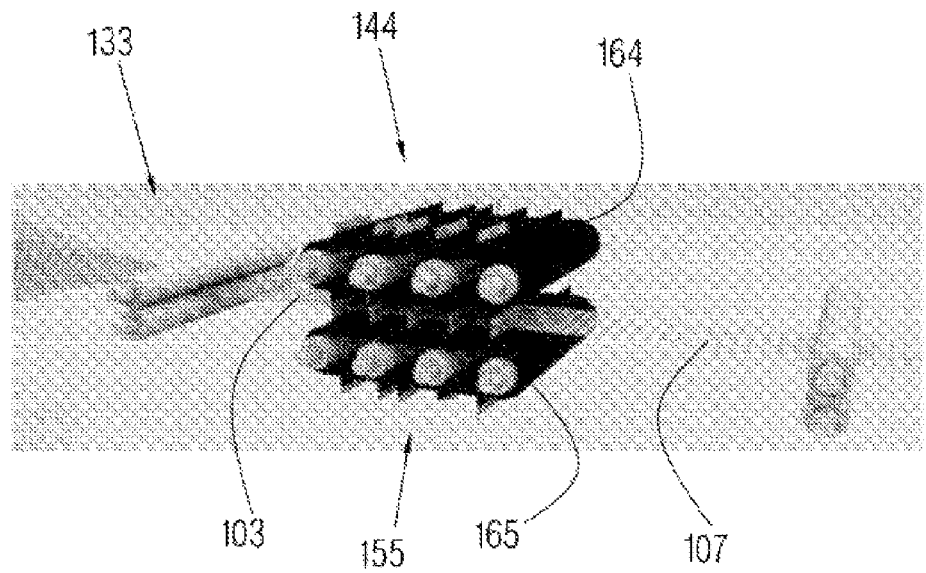
FIGS. 22 and 23 are schematic views of the roller systems in a preferred embodiment of the machine for producing plastic double-layered bags of the present invention.
Figure 23:
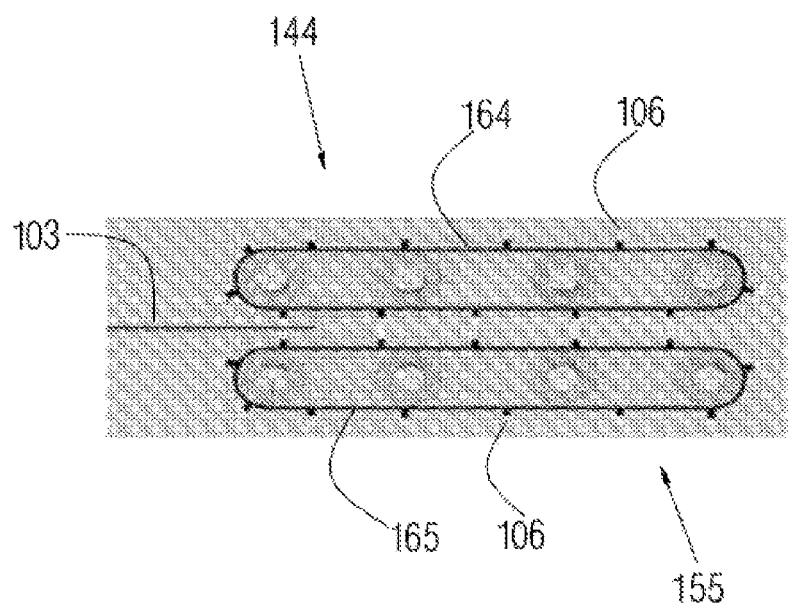
Figure 24:
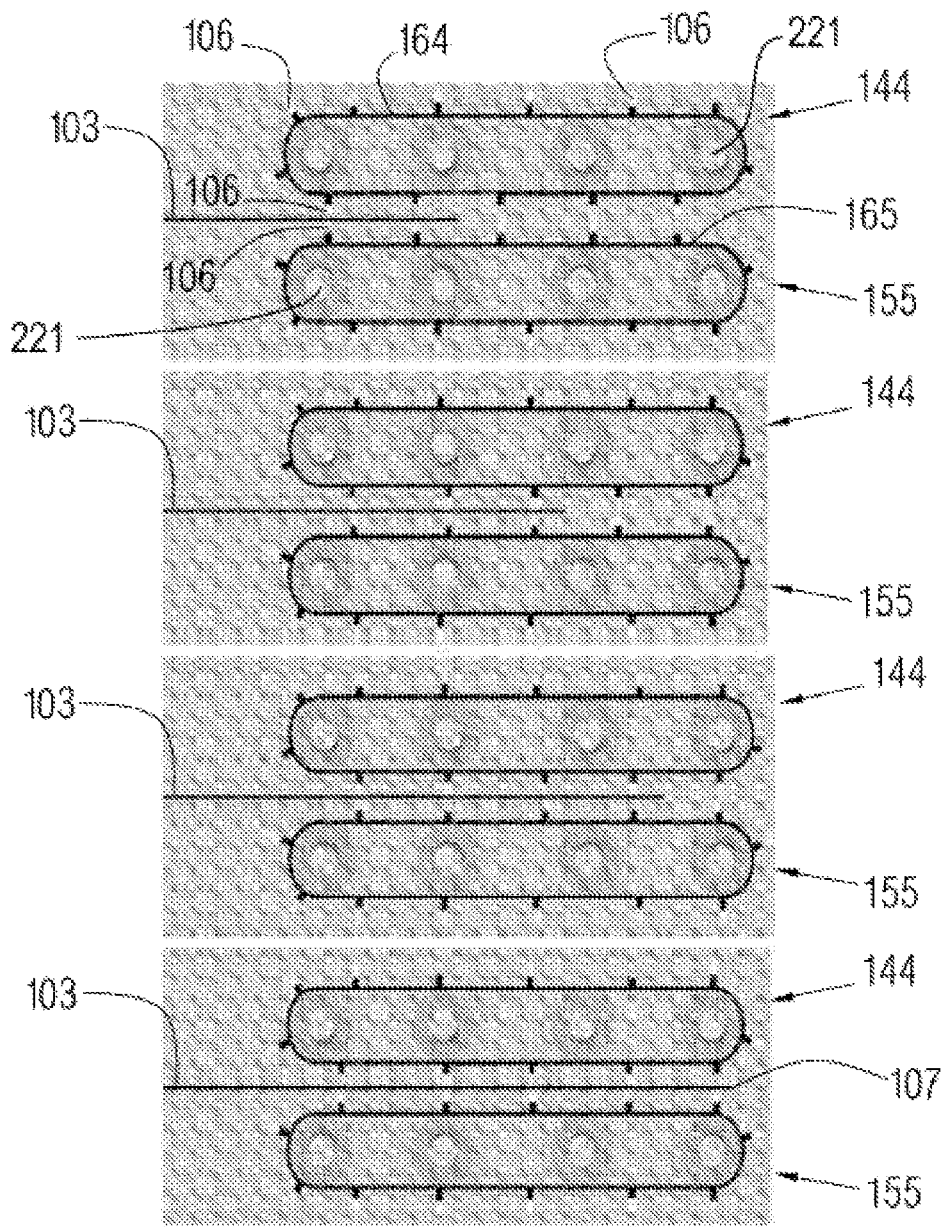
FIG. 24 shows views of successive sequences of the sealing process in a preferred embodiment of the machine for producing plastic double-layered bags of the present invention.

Said machine (FIGS. 20 and 22) make two conveyor belts (164, 165) rotate by means of rollers (221), to which several sealers using heat resistance are anchored (106), which by making contact with the plastic sheet (105), will seal the different layers and provide a double-layered bag in a single body. The sealers will be double and will be located on two conveyor belts to thereby seal the bags on the two faces thereof and thus achieve greater contact and heat to melt the different layers of the bags in the shortest time possible (FIG. 29).

More specifically, as schematically shown in FIG. 25, the machine for producing double-layered plastic bags of the present invention comprises unrolled supply means 111 of a first sheet 101 that is made of a first plastic material and unrolled supply means 122 of a second sheet 102 that is made of a second plastic material.

In this preferred embodiment, the first sheet 101 is made of low-density polyethylene (LDPE) heat shrink material and the second sheet 102 is made of high-density polyethylene (HDPE).

Moreover, the machine for producing double-layered plastic bags of the invention also comprises positioning means 133 of the two previously mentioned sheets 101, 102, already known in the state of the art.

Said positioning means 133 receive the first sheet 101 and the second sheet 102 in a continuous and unrolled manner from the same unrolled means 111, 122, respectively, and are capable of folding, bending and converting the position of said two sheets 101, 102, into a linear, folded and continuous arrangement in the resulting linear laminar assembly 103.

Said resulting linear laminar assembly 103 is made up of two central sheets 131, contiguous and overlapping resulting from a bending and folding on of the first sheet 101 over itself, and by another two outer sheets 132 resulting from another bending and folding of the second sheet 102 over itself, the two outer sheets 132 being arranged one on each side and contiguous to the other two central sheets 131, such as that which is schematically shown in FIG. 20 in a cross-sectional view of the linear laminar assembly 103.

The arrangement described implies that in the linear laminar assembly 103, the two central sheets 131 are made of low-density polypropylene (LDPE) heat shrink material and the two outer sheets 132 are made of high-density polypropylene (HDPE).

The machine for producing double-layered plastic bags of the invention also comprises two rotating roller systems 144, 155 symmetrically arranged, respectively, above and below the aforementioned resulting linear laminar assembly 103 when it comes out of the positioning means 133, as schematically shown in FIGS. 25 and 27.

Each rotating roller system 144, 155 in turn comprises a conveyor belt 164, 165, respectively, of a continuous strip arranged and installed in each roller system 144, 155 and actuated in the movement thereof by the same.

The conveyor belts 164, 165 therefore are also in a symmetric position on top of and below the aforementioned resulting linear laminar assembly 103, such that a section of the continuous cyclical movement in the roller system 144, 155 is parallel and adjacent to said resulting linear laminar assembly 102, as also shown schematically in FIG. 28.

A plurality of electric heat sealers 106 are inserted in the conveyor belts 164, 165, and therefore are movable with the same and also are symmetrically arranged above and below the aforementioned resulting linear assembly 103 that enters in the roller system 144, 155.

As shown in FIG. 28 and also in the successive sequences of FIG. 29, the heat sealers 106 are arranged on each conveyor belt 164, 165 such that in a section of the movement thereof they are in an adjacent and contiguous position with the others from the different conveyor belts 164, 165.

This takes place when, as a result of continuous and cyclical movement of the conveyor belts 164, 165, said heat sealers 106 move along the section of continuous cyclical movement of the conveyor belts 164, 165 which is parallel and adjacent to the linear laminar assembly 103 which enters in the roller systems 144, 155 as shown in FIGS. 28 and 29.

This arrangement described makes it possible so that in said section the heat sealers 106 simultaneously make contact with the linear laminar assembly 103 that enters in the roller systems 144, 155 and from each one of the opposite sides of the same linear laminar assembly 103.

Said frontal coincidence ensures contact of the different sheets 131, 132 that make up the linear laminar assembly 103 under the action of the pressing of the heat sealers 106 themselves, when the same move along the section of the continuous cyclical movement of the conveyor bets 164, 165, which is parallel and adjacent to the linear laminar assembly 113 that enters in the roller systems 144, 155.

At the same time, the heating of the heat sealers 106 carries out the sealing of the portions in contact with the sheets 131, 132 of the linear assembly 103 under the effect of the pressure of the heat sealers 106 themselves, as can be seen in the sequential representation of FIG. 29.

Figure 3:
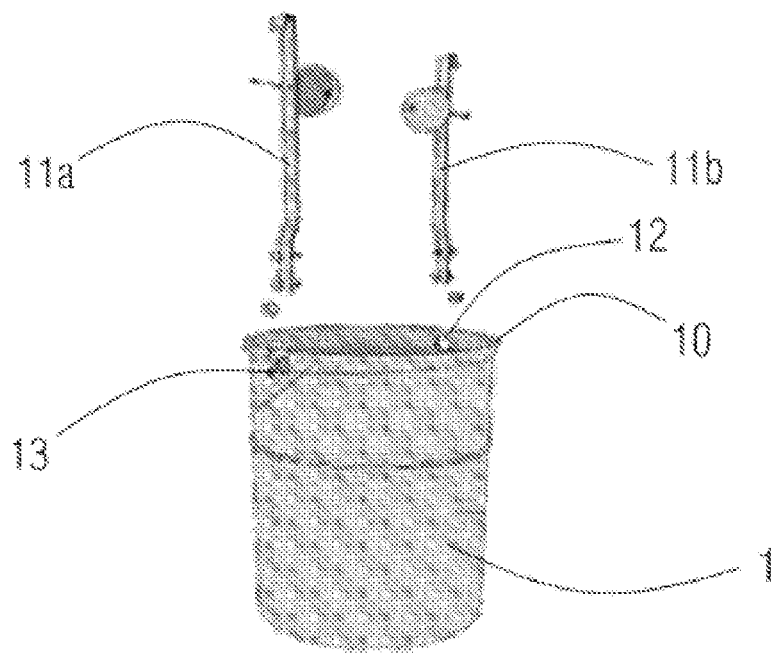
FIG. 3 is an exploded view of different mechanical elements for opening and closing the container according to the present invention.

As a result of the same, a resulting laminar strip 107 indicated in FIG. 3 and in the final sequence of FIG. 5, is obtained, also represented in FIG. 6.

Said laminar strip 107 is subsequently easily separated and individualized in different double-layered bags 108 shown in FIGS. 31 and 32, with an inner layer 181 of low-density polypropylene (LDPE) heat shrink material, and an outer layer 182 of high-density polypropylene (HDPE), which respectively correspond to the central sheets 131 and the outer sheets 132 of the previously described linear laminar assembly 103 before passing through the roller systems 144, 155 and before the sealing thereof by the heat sealers 106 of the conveyor belts 164, 165.

This explained arrangement of the machine for producing double-layered plastic bags of the invention allows the contact process of the heat sealer between the different plastic parts of the double-layered bags 108 to be more prolonged for an improved sealing without reducing the production speed of the bag.

The present invention also has the purpose of joining the plastic layers of different compositions and sealing the high-density bags by means of heat, allowing the contact process of the multiple sealers with the plastic parts of the bags to be more prolonged for an improved sealing without reducing the production speed of the bags. The contact time between the sealers and the different layers of the bag is determined by the speed of the conveyor belt and the amount of sealers installed in said belt, since the sealing time is constant.

The details, shapes, dimensions and other accessory elements, as well as the materials used to manufacture the machine for producing double-layered plastic bags of the present invention, may be suitably substituted for others which are technically equivalent, and do not diverge from the essential nature of the invention, nor the scope defined by the claims included below.

The invention claimed is:

1. A system for containing medical waste with an opening for sterilization, of those commonly used for the heating and sterilization inside a oven, characterized in that it comprises a container and a lid, a double-layered bag housed inside the container and a mechanism for opening and closing the lid of the container; the container having a threaded upper edge; the lid being provided with a rubber seal that makes the container airtight and a central inner shaft located in an axial position and arrangement and a spring that runs the length of, and concentric to, said central inner shaft and arranged on the downward side of the lid oriented towards the container, with a pushing piece on the free end of the spring and the central inner shaft being insertable in the bag; and the bag being double-layered made up of two sub-bags, one of which is housed inside the other, both sub-bags being sealed at the lateral contours thereof at the opening thereof, an inner sub-bag being made of LDPE heat shrink material and the other outer sub-bag made of high-density polyethylene (HDPE) material; and the opening and closing mechanism of the lid of the container having opening and closing capability in accordance with the heat experienced inside the oven.

2. The system for containing medical waste with an opening for sterilization according to claim 1, characterized in that the opening and closing mechanism of the lid of the container comprises two metal rods in a vertical arrangement, two holes in the upper region of the wall of the container, two lower latches-openings on the lid, another two circular latches also on the lid, and a stop on the periphery of the container on the upper region and adjacent to the upper threaded edge of the same container; said metal rods arranged diametrically opposite on the wall of the container and contiguous on the upper end to the holes of the container and secured and fastened at the lower end thereof on the inner vertical wall of the lower region of the container, and said metal rods having the greater part of the longitudinal extension thereof separated and without making contact with said inner vertical wall of the container, also being provided with protrusions on the upper end thereof of suitable dimensions for the passage thereof through the contiguous hole of the wall of the container and also provided with a suitable flexibility to move close to the inner vertical wall of the container when they are subjected to the necessary force; and the two lower latches-openings diametrically opposite and fixed to the lid, and the other two circular locks also diametrically opposite and fixed to the lid and at a higher position in relation to the two latches-openings and both pairs of elements separated by an angle approximately 20 degrees from a plan view of the lid.

* * * * *